(12) United States Patent
Csányi et al.

(10) Patent No.: US 8,716,010 B2
(45) Date of Patent: May 6, 2014

(54) SOLAR HYBRID PHOTOBIOREACTOR

(75) Inventors: István Csányi, Felső göd (HU); Laszlo Balazs, Godollo (HU); Janos Sneider, Fot (HU); Erazmus Gerencser, Budapest (HU)

(73) Assignee: GE Lighting Solutions, LLC, Cleveland, OH (US)

( * ) Notice: Subject to any disclaimer, the term of this patent is extended or adjusted under 35 U.S.C. 154(b) by 401 days.

(21) Appl. No.: 12/968,591

(22) Filed: Dec. 15, 2010

(65) Prior Publication Data

US 2012/0156762 A1    Jun. 21, 2012

(51) Int. Cl.
*C12M 1/00* (2006.01)
*C12M 3/00* (2006.01)

(52) U.S. Cl.
CPC .............. *C12M 21/02* (2013.01); *C12M 21/00* (2013.01); *C12M 23/44* (2013.01)
USPC .................. 435/292.1; 435/296.1; 435/298.1; 435/304.2; 435/304.1; 435/289.1

(58) Field of Classification Search
CPC ....... C12M 21/00; C12M 21/02; C12M 23/44
USPC .......... 435/292.1, 289.1, 296.1, 298.1, 304.1, 435/304.2
See application file for complete search history.

(56) References Cited

U.S. PATENT DOCUMENTS

| | | | |
|---|---|---|---|
| 2004/0259239 A1* | 12/2004 | Branson et al. | 435/292.1 |
| 2010/0255458 A1* | 10/2010 | Kinkaid | 435/3 |
| 2011/0070632 A1* | 3/2011 | Katoch et al. | 435/292.1 |
| 2011/0117638 A1* | 5/2011 | Veres et al. | 435/292.1 |
| 2012/0115209 A1* | 5/2012 | Loubiere et al. | 435/257.1 |
| 2012/0171733 A1* | 7/2012 | Im et al. | 435/101 |
| 2012/0288921 A1* | 11/2012 | Yuan et al. | 435/287.1 |

* cited by examiner

*Primary Examiner* — Nathan Bowers
(74) *Attorney, Agent, or Firm* — Fay Sharpe LLP

(57) ABSTRACT

A photobioreactor system is provided that comprises a bioreactor including at least two bioreactor tubes, each having an end and a hollow interior, the ends being connectively joined by one or more connector units having a hollow portion defined by a circumference, a solar concentrator configured to collect and concentrate solar power, at least one light guide associated with the solar concentrator to illuminate the hollow portion of the one or more connector units, and at least one LED illuminating the one or more connector units.

15 Claims, 7 Drawing Sheets

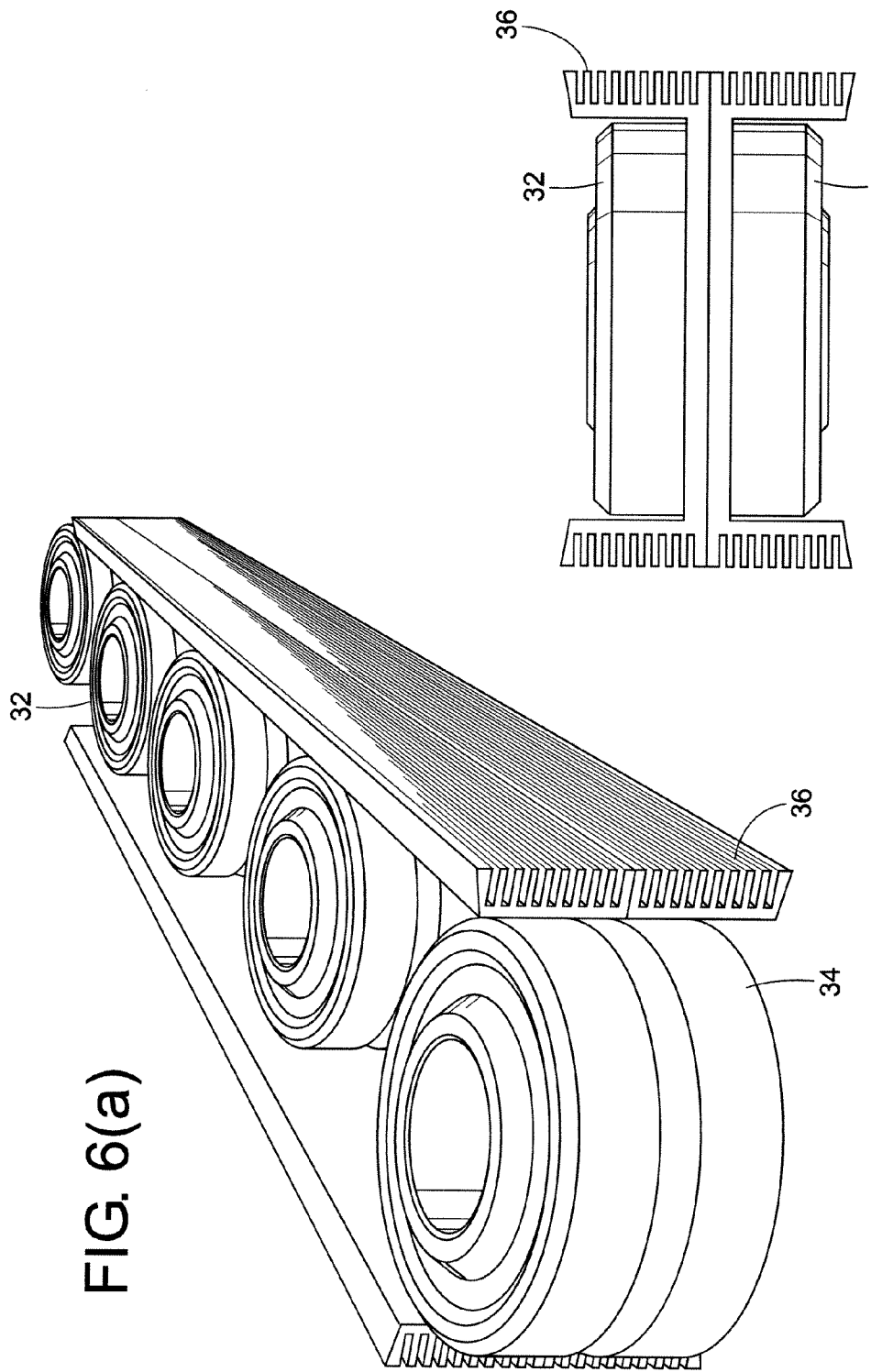

SOLAR HYBRID PHOTOBIOREACTOR

BACKGROUND

The present exemplary embodiments relate to photobioreactors. They find particular application in conjunction with optimizing the illumination of photobioreactors by combining a solar collector light guide system with LED lighting, and will be described with particular reference thereto. However, it is to be appreciated that the present exemplary embodiments are also amenable to other like applications.

Photobioreactors are enclosed culture vessels designed for controlled biomass production of phototrophic liquid cell suspension cultures, such as algae. Photosynthetic organisms, like algal biomasses have several rapidly growing applications such as, for example, use as an energy source, food supplements, cosmetic additives, pigment additives, and pollution control agents. Algal biomasses are also very useful in the production of biofuel, a typically non-toxic and biodegradable environmentally safe alternative to conventional fuel.

Photobioreactors offer many advantages over open systems, such as preventing or at least minimizing contamination, offering better control over cultural conditions (pH, carbon dioxide, temperature), preventing water evaporation, lowering carbon dioxide losses, and permitting higher cell concentrations. For successful cultivation, algae needs light, nutrients and mixing, while shear forces and high oxygen levels should be avoided. Algal culture systems can be illuminated by artificial light, solar light, or both. A difficult feature for photobioreactors to provide is an even distribution of light at a proper intensity throughout the bioreactor. Generally, in most systems, ideal light intensities occur only in a very small part of the bioreactor. Often, inside the culture, light cannot penetrate because of cell shading and microalgae are subjected to darkness. The photobioreactor walls may experience dramatic drops in photosynthesis yield due to photoinhibition and heat dissipation caused by too high light intensities. Photoinhibition is the light induced reduction in the photosynthetic capacity of a plant, algae, or cyanobacterium.

Many different types of photobioreactors exist, such as tubular reactors, flat panel reactors, vertical column reactors, and bubble column reactors. Typically, tubular photobioreactors are widely used for the mass cultivation of algae. Most tubular photobioreactors are usually constructed with either glass or plastic tubes and can be in the form of horizontal/serpentine, vertical, conical, or inclined, for example, to maximize sunlight capture. Tubular photobioreactors are preferred for outdoor mass cultures of algae since they have large illumination surface area. However, photoinhibition is very prevalent in tubular photobioreactors when the reactors are scaled up by increasing the diameter of the tubes, since the illumination surface to volume ratio decreases. Additionally, the productivity of the photobioreactor is limited to the intensity of the sun, which itself depends on the time of day, season, the localization and the diurnal cycle. It is possible to provide an artificial light to compensate for the periods of low intensity. However, the use of artificial light can be very costly and requires a large amount of energy usage. Therefore, it may be desirable to maximize crop yield by combining concentrated solar energy with photovoltaic cell-battery powered LED lighting to maintain optimum light level for biomass production throughout the day.

Several photobioreactor designs have been developed to try to harness solar energy. U.S. 2009/0047722 discloses including, within a bioreactor system, a solar energy system that collects and/or supplies sunlight, as well as direct light into the bioreactor. The solar collector is coupled to the lighting system, which comprises a network of fiber optic waveguides and optical switches to route, guide, and eventually emit at least a portion of the light collected by the solar collector toward at least some of the algae within the bioreactor. The reactor is illuminated from the exterior surface. U.S. Pat. No. 6,603,069 teaches a full spectrum solar energy system that uses a hybrid solar concentrator that collects, separates, and distributes the visible portion of sunlight, while simultaneously generating electricity from infrared portion of the spectrum. The disclosed system also implements large-core polymer optical fibers to deliver large quantities of visible sunlight into photobioreactors.

Additionally, photobioreactors have been created for use solely with artificial light sources. U.S. Pat. No. 5,614,378 describes a photobioreactor system for a closed ecological life support system including, for example, an optical transmission system, uniform light distribution, and continuous cycling of cells. The optical transmission system illuminates the reactor internally and includes a light source which is external to the reactor preventing heat generation problems. The light source may by any conventional light source and filters may be utilized to eliminate undesired wavelengths.

Generally artificial light sources in photobioreactors consist of high pressure sodium (HPS) and/or fluorescent lamps. However, these light sources are problematic for plant cells. HPS lamps must be placed a safe distance from the algae to avoid over-lighting and potential burning of the plant cells. Additionally, although HPS lamps provide high light output, the lighting level is not uniform along the tube. Most significantly however, is that both HPS and fluorescent lamps produce light on wavelengths which plants cannot absorb to use as an energy source.

Therefore, a need exists for a bioreactor design that can combine a solar collector-light guide system with a photovoltaic cell-LED lighting system to fully optimize the illumination level and distribution.

BRIEF DESCRIPTION

In accordance with one aspect of the present disclosure, a photobioreactor system is provided. The photobioreactor comprises a bioreactor including at least two bioreactor tubes, each having an end and a hollow interior, the ends being connectively joined by one or more connector units having a hollow portion defined by a circumference, a solar concentrator configured to collect and concentrate solar power, at least one light guide associated with the solar concentrator to illuminate the hollow portion of the one or more connector units, and at least one LED illuminating the one or more connector units.

In accordance with another aspect of the present disclosure, a photobioreactor system for growing algae is provided. The photobioreactor includes a bioreactor having at least two light transmissive tubes for housing a slurry of algae, at least one LED assembly positioned directly on at least one of the one or more light transmissive tubes, wherein the LED assembly comprises a first substantially linear array of LED chips and second substantially linear array of LED chips, disposed below the first array, and a heat sink coupled to the at least one LED assembly.

In accordance with yet another aspect of the present disclosure, a method for optimizing the illumination level in a photobioreactor is provided. The method includes joining at least a first bioreactor tube with a second bioreactor tube using at least one connector unit to form a bioreactor, collecting and concentrating solar energy with a solar concentrator, transporting the solar energy to the at least one connector unit using one or more light guides for illuminating the bioreactor, converting solar energy to electrical energy using a photovoltaic cell, storing the electrical energy in a means for storing electrical energy, associating at least one LED with the at least one connector unit, the at least one LED being connected to the means for storing electrical energy, and energizing the at least one LED when the solar energy is insufficient, causing the at least one LED to illuminate the bioreactor.

BRIEF DESCRIPTION OF THE DRAWINGS

FIG. 6a is a top side view of a first and second LED array-heat sink arrangement according to another aspect of the present disclosure;

FIG. 6b is a side view of a first and second LED array-heat sink arrangement according to another aspect of the present disclosure;

DETAILED DESCRIPTION

Figure 1:
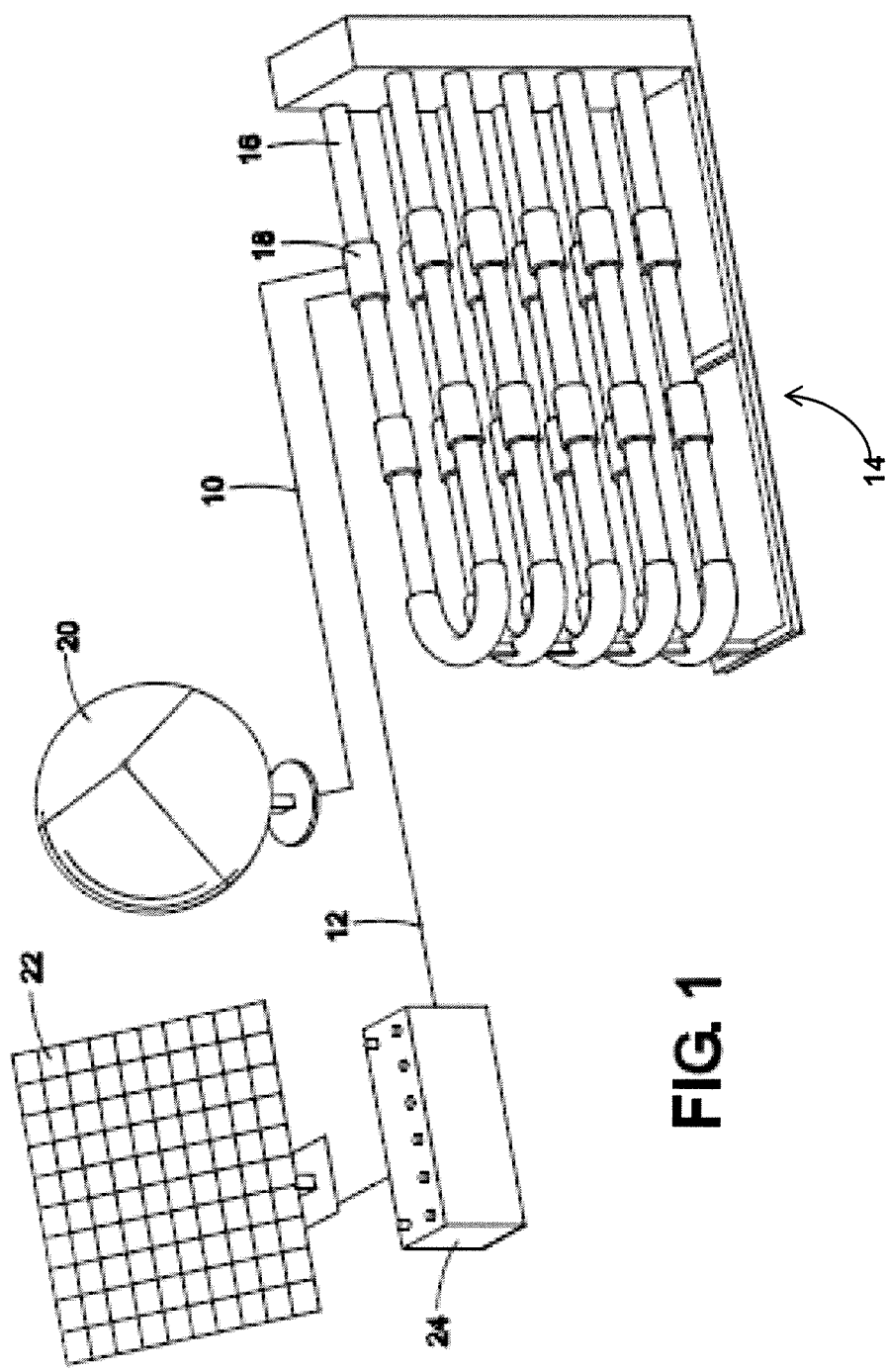
FIG. 1 is a conceptual diagram of the photobioreactor system according to one aspect of the present disclosure.
Figure 2:
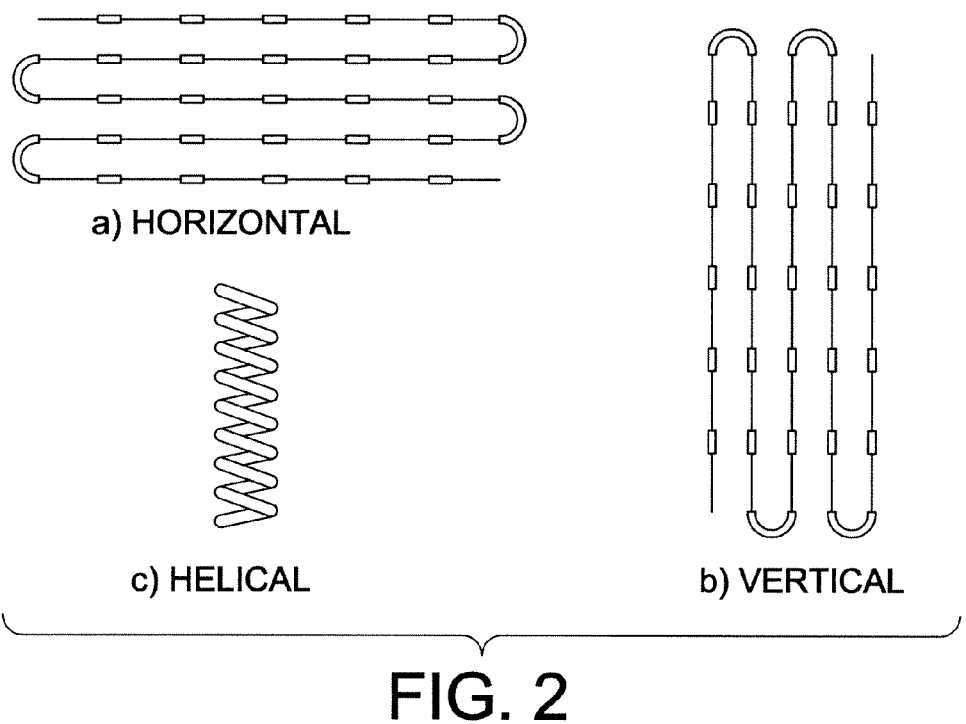
FIGS. 2(a)-(c) are examples of the various possible orientations for the photobioreactor according to the present disclosure.

FIG. 1 illustrates one embodiment of the bioreactor system with optimized illumination levels. The system employs a method that can maximize the light in-coupling efficiency from both the light guide 10 and the LED 12 to the bioreactor 14. The bioreactor 14 will be described herein as a tubular bioreactor; however, any known bioreactor may be substituted. Tubular bioreactors are generally constructed from either glass or plastic tubes and cultures are circulated throughout the reactor, preferably with the use of a pump or an airlift system. The bioreactor 14 according to one embodiment comprises transparent or translucent tubes 16 connected with connector units 18. A connector unit 18 accommodates the ends of two bioreactor tubes 16 to provide an undisturbed flow of algal slurry through the tubes and an appropriate watertight sealing for the bioreactor assembly. The connector units 18 enable a compact reactor design. The arrangement of the tubes can be horizontal, vertical, helical, or other configurations determined by the shape of the tubes and the connecting elements, as illustrated in FIG. 2.

According to one aspect, light may be delivered to the bioreactor using two parallel channels. The first channel comprises one or more light guides 10 that connect a solar power concentrator 20 to a connector unit 18 that joins adjacent bioreactor tubes 16 and redistributes the light to throughout the bioreactor 14. The concentrator 20 collects and concentrates solar energy and the light guides 10 transport the harnessed solar light to the bioreactor 14. Solar energy may be collected and concentrated using various conventional methods. One exemplary method is to use a parabolic trough, which consists of a linear parabolic reflector that concentrates light into a receiver positioned right above a parabolic mirror. Another exemplary method for solar energy collection is through use of linear fresnel reflectors, which consist of many thin mirror strips, rather than of parabolic mirrors to concentrate sunlight onto two tubes with working fluid. Alternatively, the solar energy may be collected using a stirling dish that consists of a standalone parabolic reflector that concentrates light onto a receiver positioned at the reflector's focal point, or a solar power tower that uses an array of tracking reflectors to concentrate light on a central receiver atop a tower. The direct solar illumination channel may further incorporate optical filters, absorbers, etc. to select the optimal spectrum for alga cultivation or attenuate the light intensity.

However, to maximize a crop yield, algae should be exposed with a constant light level. During daylight, the light guide transfers solar light to the bioreactor 14. At times daylight is not available; however, the bioreactor system may additionally include a second source of illumination from one or more LEDs 12. An indirect illumination channel is provided that includes a photovoltaic (PV) cell 22 connected to a means for storage of electrical energy 24, such as one or more batteries, capacitors, supercapacitor, and flow batteries. In general the means for storage may comprise electrical, electrochemical, chemical, mechanical, and thermal storage. During daylight, the PV cell 22 converts solar energy to electrical energy, and stores this energy in the battery 24. In the evening, when natural light is unavailable, the charged battery provides power to one or more LEDs coupled to the connector unit 18 of the bioreactor 14. Accordingly, when direct solar illumination drops to a suboptimal level, such as when the sun begins to set or when the sun is hidden by clouds, a control circuit (not shown) may switch on the LED (s) 12 to supplement or take over for the direct solar illumination while the supply is decreased.

Figure 3:
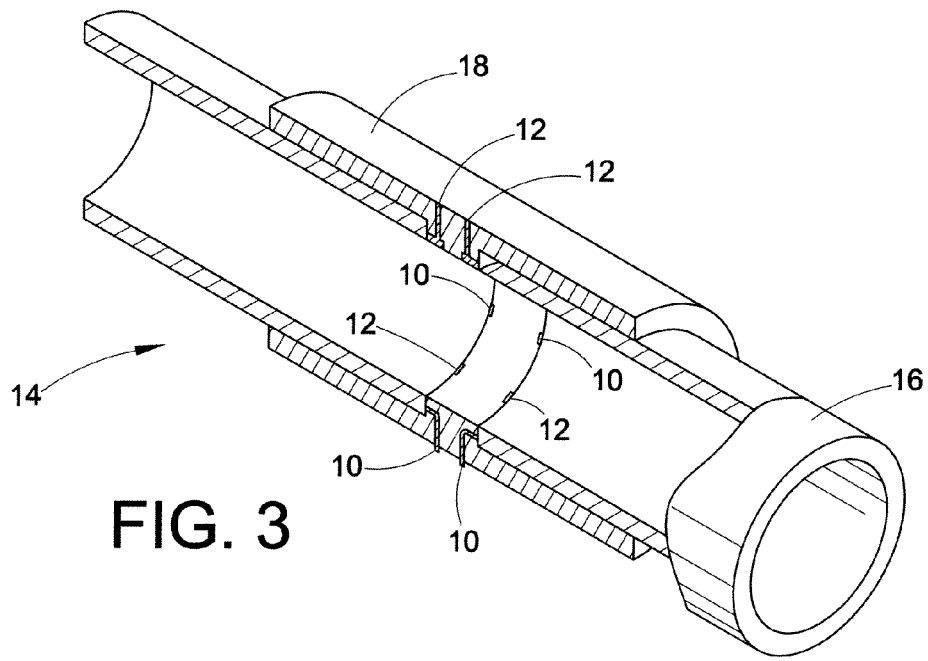
FIG. 3 is a side and cross-sectional view of a connector unit of the photobioreactor system.
Figure 4:
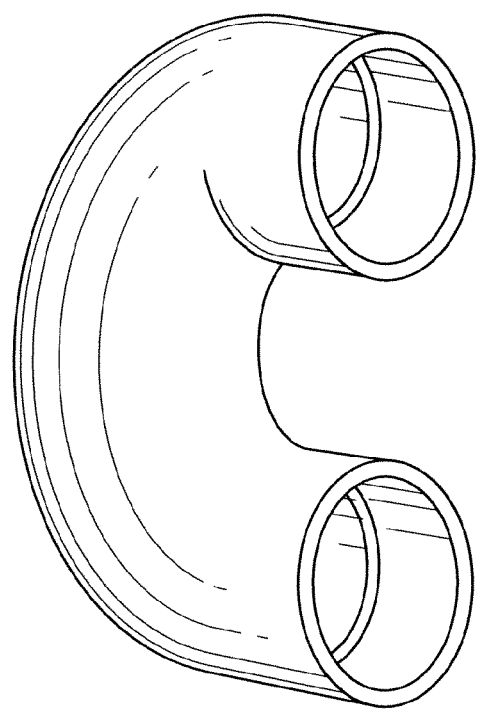
FIG. 4 is a front side view of a curved connector unit according to another aspect of the present disclosure.

FIG. 3 illustrates one embodiment of the tube connector unit 18. The tube connector unit 18 enables the optimization of the light in-coupling efficiency from the LED 12 and from the light guide 10 to the tubular bioreactor. The connector unit 10 may be a straight extender or can have a bent or curved shape incorporating any angle necessary depending on the particularly desired shape of the bioreactor. FIG. 4 illustrates a connector unit 18 having a curved shape. The connector unit 18 receives one end of the LEDs and/or light guides, with the other end of the respective LED and light guide being connected to the solar collector.

Figure 5:
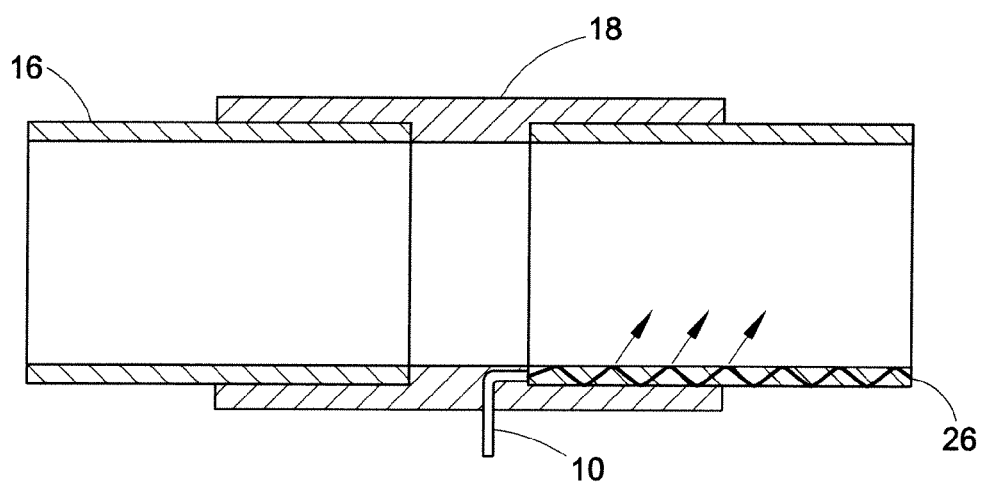
FIG. 5 is a schematic representation of the light re-distribution in the reaction tube according to another aspect of the present disclosure.

The LEDs 12 and light guides 10 may be arranged in an alternating manner around the inside circumference of the connector unit 18, as illustrated in FIG. 3. The LEDs 12 and light guides 10 may be incorporated into the connector unit 18 and then fed into the rim of the bioreactor wall 26. Each of the LEDs 12 and light guides 10 are fed into the bioreactor wall 26 such that they face the interior rim of the bioreactor tube 16 and direct illumination into the hollow middle of the tube. As displayed in FIG. 5, the wall 26 of the bioreactor tube 16 is designed to allow transmission of the light along the tube wall 26 via successive reflection due to the difference in the refractive index of the tube and that of the surrounding medium. The inner surface of the tube may be modified at various locations to allow for re-distribution of the light into the tube interior. For instance, the tube may be modified by, for example, 1)

modifying the surface morphology of the inner tube (ramified surface), 2) adding a refractive index matching layer using a material different from the material of the tube, and a combination of 1) and 2). Uniform illumination of the algal slurry is achieved by optimizing one or more of the distance between the neighboring connecting units, the diameter of the reactor tube, the number and power of the LEDs 12, and the solar light intensity transferred by the light guides 10.

Figure 7A:
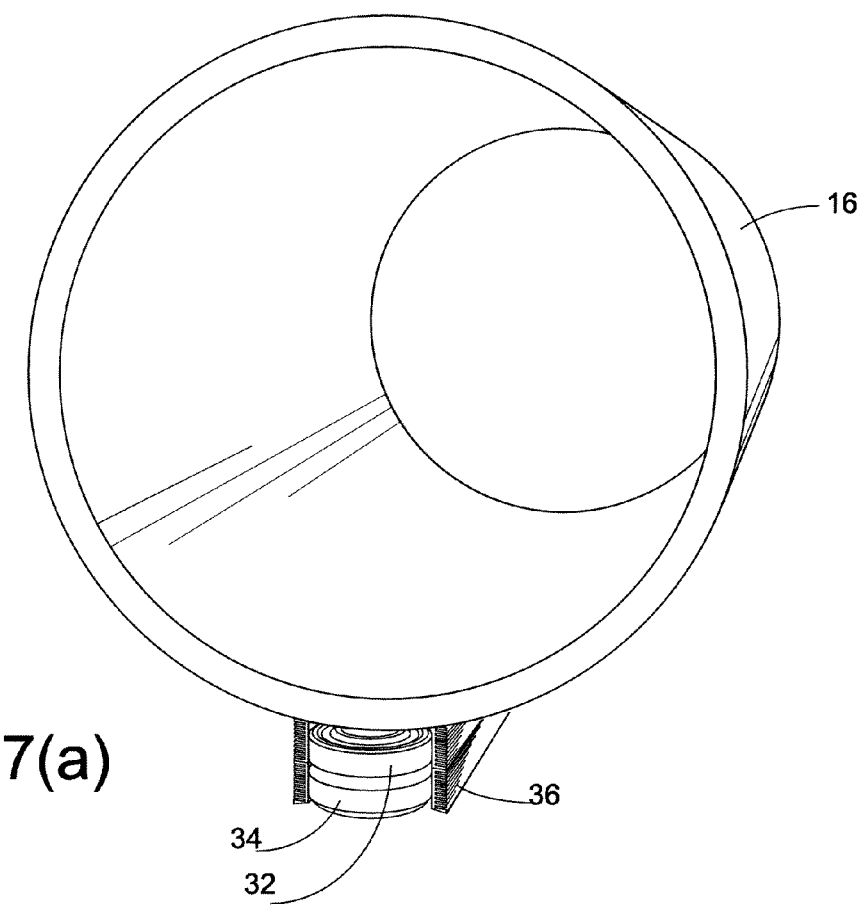
FIG. 7(a) is a front perspective view of a bioreactor tube and LED assembly according to another aspect of the present disclosure.
Figure 7B:
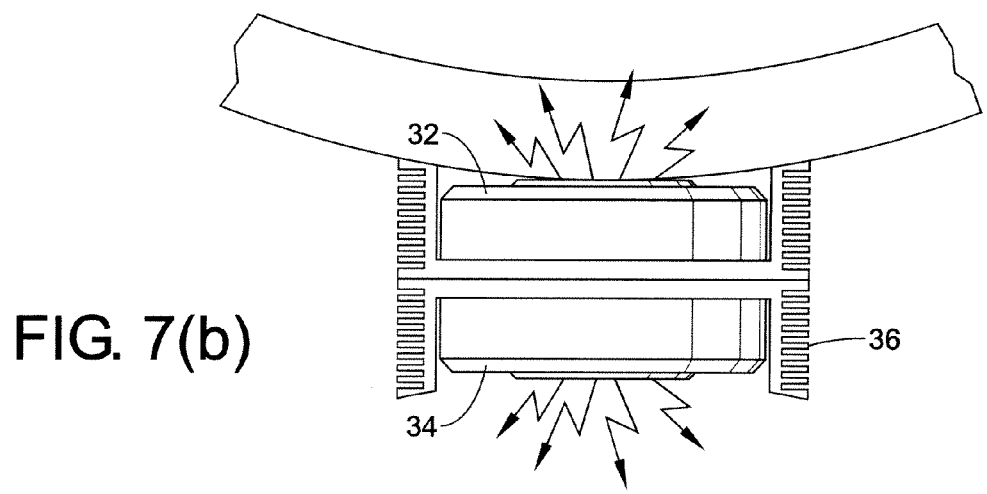
FIG. 7(b) is a front view of a bioreactor tube and LED assembly according to another aspect of the present disclosure.

According to another aspect, the LEDs may form an assembly to be attached to the outside of the tube surface. FIGS. 6(a) and (b) illustrate an LED assembly configuration comprising a first substantially linear LED array 32 and a second substantially linear LED array 34 disposed below the first substantially linear LED array 32. Each of the first 32 and second 34 LED arrays may comprise multiple LED chips 12. The first and second LED arrays 32, 34 are connected to a heat sink 36, which extends along the sides of and in between the first and second LED arrays. The heat sink is generally shaped in an "H" configuration, with the two vertical sides having comb-like projections extending away from the heat sink. The heat sink 36 attaches the first LED array 32 to an exterior side of the bioreactor rector tube (FIG. 7(a),(b)) in the bioreactor system. The heat sink 36 helps to secure the first LED array 32 to the tube, such that the LED chips radiate light directly into the tube 16 (FIG. 7(b)), or alternatively radiate the light at any desired angle. Since the second LED array 34 is disposed below the first LED array 32, in the event a bioreactor tube arrangement is such that a second bioreactor tube is disposed below the first bioreactor tube the second LED array 34 may attach to the outside of the second tube (not shown). If the first LED array 32 is attached to the exterior bottom of the first bioreactor tube, the second LED array attaches to the exterior top portion of the second bioreactor tube. As such, the second LED array 34 may radiate light to the bioreactor tube below the tube where the first LED array 32 is attached (FIG. 7(b)). Preferably, the first and second tubes 16 are connected via the connector units described above, such that the second LED array creates a secondary light source for the bioreactor 14 as a whole. This arrangement may be implemented on bioreactors having any number of individual tubes connected such that tubes are disposed in a close succession.

Similar to feeding the LEDs into the tube wall as described above, attaching the LEDs directly onto the surface of the bioreactor tubes minimizes the loss of light while maximizing heat transfer to the water through the glass. The LED/heat sink arrangement is placed directly on the tubes to ensure there are no air-gaps and thus no loss of photons. An additional benefit of this arrangement is that the LED/heat sink package is small enough such that it does not cast a shadow on the tubes during times of natural sunlight. Accordingly, it is not necessary to remove these light sources during the daylight as is customarily the case with fluorescent lighting systems. The LED array packages may be produced in different lengths and may be coupled together to allow for tube covering as long as 30 feet, for example.

Figure 8:
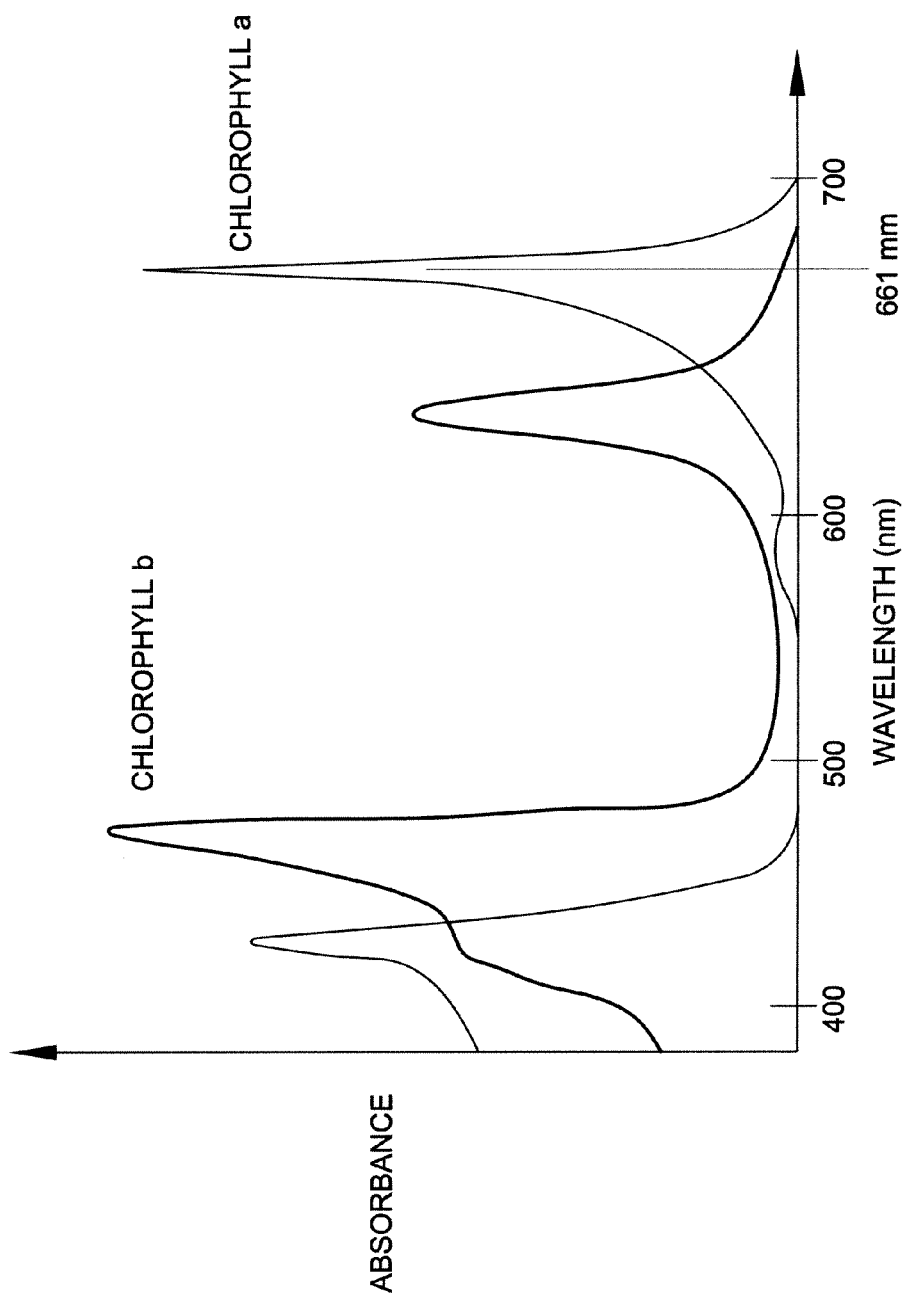
FIG. 8 is a graphical representation of the absorption peaks for chlorophyll a and b.
Figure 9:
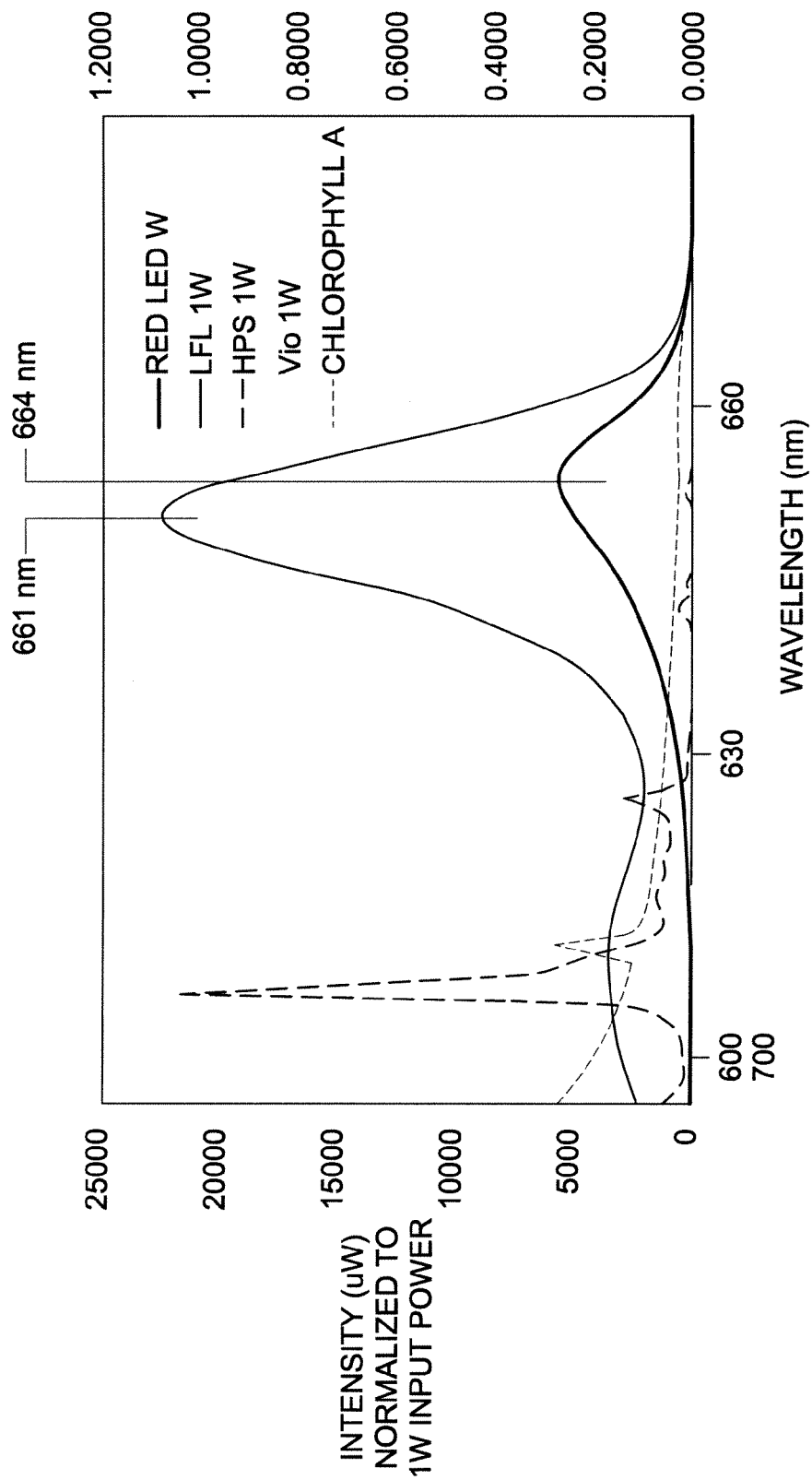
FIG. 9 is a graphical representation of the absorption peak of chlorophyll a and various light sources.

In the above photobioreactor system configurations, the light sources radiate photons into the bioreactor tubes, where the photons are then mixed and flow with the water and other solid particles. The algae then transform the light photons from the light sources into plant nutrition, carbon-dioxide and water. Preferably, the light sources are designed to radiate light in the peak wavelength ranges that can be absorbed by the algae or other biomass. A peak wavelength is the single wavelength where the radiometric emission spectrum of the light source reaches its maximum. The light sources' peak wavelength should match the wavelengths where the algae have the highest absorbance peaks, which are illustrated in FIG. 8. As shown in the graph of FIG. 8, the absorbance peaks for chlorophyll a, b, c1, c2 and d vary, and therefore, the desired wavelength will vary depending on the algae. Every species of algae contains chlorophyll a, which has a peak absorbance at a wavelength of about 661 nm+/−5 nm. Chlorophyll b, which is found in green algae, has its maximum absorption peak at about 453 nm. As such, it is desirable to tune the light source to radiate at a wavelength that corresponds to the particular type of biomass sought to be cultured. In the case of chlorophyll a, the light source should be tuned to radiate at a wavelength as close to 661 nm as possible. As illustrated in FIG. 9, a 1 W red LED experiences a high intensity peak around 664 nm, within the desired wavelength range of chlorophyll a. In contrast, none of the peak wavelengths of LFL at 1 W, HPS at 1 W and Vio at 1 W are within the range of chlorophyll a. Accordingly, the use of a red LED in the present bioreactor system would allow for optimal absorption by chlorophyll a.

The bioreactor system may be equipped with photon flux sensors and dimmable drivers (not shown) to compensate for decreasing natural sunlight during the day and at dusk and dawn. The sensors facilitate constant and automatic adjustment of the intensity of the LEDs 12 to keep a constant illumination level inside the reactor tube 16. This provides a significant advantage over conventional systems that are either not dimmable, or only have limited potentials depending on the gear system. The photon flux sensors distribute the photons along the tube ensuring that the algae can get a uniform level of photon flux density.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A photobioreactor system comprising:
    a bioreactor including at least two bioreactor tubes, each having an end and a hollow interior defined by a circumferential wall, said ends being connectively joined by one or more connector units, said connector units having a hollow portion defined by a outer wall;
    a solar concentrator configured to collect and concentrate solar power;
    at least one light guide associated with said solar concentrator;
    at least one LED assembly; and
    wherein said light guide and said LED assembly are positioned in said one or more connector units to face a rim of said bioreactor tube circumferential wall, introduce light into said rim, and provide transmission of light along said circumferential wall, said circumferential wall providing re-distribution of the light into the hollow interior of the bioreactor tubes.

2. The bioreactor according to claim 1, wherein said one or more connector units are configured to connect said at least one of said light guide and said LED to said bioreactor tubes.

3. The bioreactor system according to claim 1, wherein said LED assembly is in electrical communication with a photovoltaic cell connected to a means for storing electrical energy.

4. The bioreactor system according to claim 3, wherein said photovoltaic cell is configured to convert solar energy into electrical energy.

5. The bioreactor system according to claim 4, wherein said means for storing said electrical energy comprises a battery.

6. The bioreactor system according to claim 5, wherein said at least one LED assembly is powered by the electrical energy stored in said battery.

7. The bioreactor system according to claim 1, further including a control circuit configured to activate the at least one LED assembly.

8. The bioreactor system according to claim 1, wherein said at least one LED assembly and light guide are positioned in an alternating manner around the circumference of the one or more connector units.

9. The bioreactor system according to claim 1, wherein one or more connector units comprise one of a straight, bent, and curved shape.

10. The bioreactor system according to claim 1, wherein said at least one LED assembly radiates light at a wavelength between about 656 nm and 666 nm.

11. The bioreactor system according to claim 1, including a further LED assembly comprised of a first substantially linear array of LED chips and a second substantially linear array of LED chips, disposed below said first linear array a heat sink coupled to said at least one LED assembly; and wherein said LED assembly is connected to a first bioreactor tube by said heat sink, said first array of LED chips being positioned to radiate light directly into said first bioreactor tube.

12. The bioreactor system according to claim 11, wherein said LED assembly is connected to a second bioreactor tube, disposed below said first bioreactor tube, by said heat sink, said second array of LED chips being positioned to illuminate said second bioreactor tube.

13. The bioreactor system according to claim 1, further including a control circuit configured to activate said LED assembly when said solar power is insufficient.

14. The bioreactor system according to claim 11, wherein said LED assembly radiates light at a peak wavelength within the algae's highest absorption range.

15. The bioreactor system according to claim 14, wherein said LED assembly radiates light at a peak wavelength between about 656 nm and 666 nm.

* * * * *